United States Patent [19]
Hatch et al.

[11] Patent Number: 5,468,641
[45] Date of Patent: Nov. 21, 1995

[54] DEVICE FOR VALIDATING UROBILINOGEN TEST DEVICES

[75] Inventors: Robert P. Hatch, Elkhart; Marilyn J. Radtke, South Bend, both of Ind.

[73] Assignee: Bayer Corporation, Elkhart, Ind.

[21] Appl. No.: 238,003

[22] Filed: May 3, 1994

Related U.S. Application Data

[63] Continuation-in-part of Ser. No. 72,441, Jun. 7, 1993, abandoned.

[51] Int. Cl.$^6$ .......................... G01N 33/48; G01N 33/72
[52] U.S. Cl. .................. 436/97; 436/166; 422/56
[58] Field of Search .................. 422/56; 436/166, 436/12, 63, 97, 99

[56] References Cited

U.S. PATENT DOCUMENTS 4,405,718  9/1983  Rapkin et al. .......................... 436/8

Primary Examiner—Lyle A. Alexander
Attorney, Agent, or Firm—Jerome L. Jeffers

[57] ABSTRACT

The present invention involves the use of certain indole sulfonates in a test control method for the Ehrlich reagent used in diagnostic tests for urobilinogen. The indole sulfonates exhibit unique solubility characteristics which facilitate their application to dry carrier matrixes with subsequent rehydration during their use in the test control method.

14 Claims, No Drawings

DEVICE FOR VALIDATING UROBILINOGEN TEST DEVICES

BACKGROUND OF THE INVENTION

This application is a continuation-in-part of application Ser. No. 08/072,441, filed on Jun. 7, 1993 now abandoned.

Various disease conditions such as hemolytic and hepatic diseases, biliary obstruction and other bile duct dysfunctions are known to cause abnormally high levels of urobilinogen in urine.

The standard method for detecting urobilinogen in urine employs the Ehrlich reaction which utilizes an aqueous solution of p-dimethylaminobenzaldehyde and hydrochloric acid, often referred to as Ehrlich's reagent. In the presence of urobilinogen, there is produced a complex with the Ehrlich reagent which exhibits absorption in the visible spectrum. The color produced can be one of various shades of reddish-brown, depending on the presence of interfering substances in the urine sample such as p-aminosalicylic acid, porphobilinogen and urea.

Currently available dip and read reagent strips can incorporate Ehrlich's reagent, i.e. p-dimethylaminobenzaldehyde and hydrochloric acid. Such strips are dipped into urine whereupon the color developed is compared with a standard color chart prepared for use in conjunction with the reagent strips to determine the presence of and approximate concentration of urobilinogen.

It is customary to use control solutions which are capable of producing the same color reaction as that produced by the presence of urobilinogen to check the instrument used to read the test strip, or, if the test involves human visual observation, in checking the skill of the technician in carrying out the test. Such controls are also useful for educational purposes such as instructing technicians in how best to carry out urobilinogen tests.

In Analytical Biochemistry, 8, 75–81 (1964) there is described the ability of indole and tryptophan to form colored products by reacting with p-dimethylaminobenzaldehyde. The indoles disclosed in this reference have been used as urobilinogen control reagents since they react with Ehrlich's reagent to produce reddish-brown colors which closely resemble colors formed by the reaction of urobilinogen in urine and Ehrlich's reagent. Indoles having improved water solubility would be desirable since a more soluble indole enables the preparation of a more concentrated impregnation solution enabling the incorporation of a sufficient amount of the indole into an absorbent reagent strip. Furthermore, a more soluble indole facilitates its reconstitution from the reagent strip into the test solution at a suitable concentration.

U.S. Pat. No. 4,405,718 discloses the use of indoles characterized by the formula:

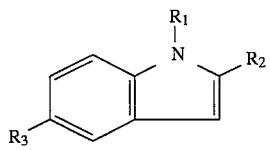

where $R_1$ and $R_2$ are H or unsubstituted $C_1$–$C_4$ alkyl and $R_3$ is H, unsubstituted $C_1$–$C_4$ alkyl, unsubstituted $C_1$–$C_4$ alkoxy or halogen in a non-ionic detergent as a urobilinogen control standard. While this formulation provides the desired color response, the indoles are not sufficiently water soluble for use as the control reagent and must, therefore, be mixed with the nonionic surfactant, before they can be used. The indole/nonionic surfactant formulation is not suitable for use in the type of format where the control reagent is simply absorbed in a strip of bibulous material which is placed in an aqueous environment to provide the amount of indole necessary for testing the Ehrlich solution in the urobilinogen test strip.

SUMMARY OF THE INVENTION

The present invention involves a test control method for a reagent system containing p-dimethylaminobenzaldehyde. The method involves combining the reagent system in aqueous solution with a 2-methylindole of the formula:

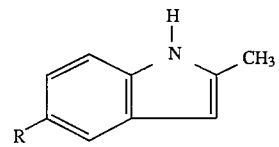

where R is $-(CH_2)_n SO_3^-$ wherein n is 2 to 6 (preferably 2 to 4) or $-[OCH_2-(CH_2)_x-]_m SO_3^-$ wherein X is 2 or 3 and m is 1 or 2. The presence of the p-dimethylaminobenzaldehyde is confirmed by a detectable color change.

The sulfonated indole is typically provided in the form of a strip of a matrix of bibulous or nonbibulous material bearing an adequate quantity of the indole control composition.

DESCRIPTION OF THE INVENTION

The urobilinogen control standards of the present invention can be used in the form of their aqueous solution by simply immersing a reagent strip containing p-dimethylaminobenzaldehyde and hydrochloric acid in the solution and determining if the expected color change takes place. Typically, the indoles of the present invention can be embodied in a carrier in the form of a pressed or molded tablet containing a conventional carrier material and the indole. In a preferred embodiment, the indoles can be incorporated into a carrier matrix and used in the strip format. The term carrier matrix is intended to refer to bibulous and non-bibulous matrices which are insoluble in and maintain their structural integrity when exposed to water or physiological fluids. Suitable bibulous matrices which can be used include paper, cellulose, wood and synthetic resin fleeces as well as woven and nonwoven fabrics. Thus, by selecting a carrier matrix impregnated with one or more of the sulfonated indoles of the present invention, there is provided a convenient method for introducing the indole into the test solution by simply dipping the indole containing strip into a water supply. The unique solubility characteristics of the sulfonated indoles which are useful in the present invention facilitate their use in this format since they will readily dissolve from the carrier matrix to provide an aqueous solution suitable for testing the Ehrlich composition in the test strip.

The sulfonated indoles of the present invention are represented by the formula:

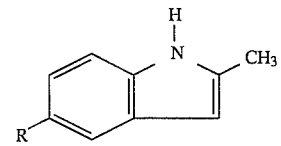

In the above formula, R is $-(CH_2)_n SO_3^-$ where n is 2 to 6 or $-[OCH_2-(CH_2)_x-]_m SO_3^-$ wherein X is 2 or 3 and m is 1 or 2. These alkyl and alkylether sulfonates exhibit the desired solubility properties while maintaining the ability of their precursors to form a colored complex with the p-dimethylaminobenzaldehyde of the Ehrlich reagent.

The invention is further illustrated by the following examples:

EXAMPLE I

Preparation of 2-Methyl-5-(4-sulfonatobutoxy)indole a) 5-hydroxy-2-methylindole

To a −65° C. solution of 8.6 g (53.4 m mol) 5-methoxy-2-methyl indole in 110 mL of $CH_2Cl_2$ was added dropwise 30.4 g (117 m mol) of boron tribromide. The reaction was allowed to warm to room temperature and stirred for 30 minutes. After cooling the mixture to 5° C., 200 mL of 50% water/chloroform was cautiously added. The aqueous layer was separated and the pH adjusted to 5.8 with aqueous sodium hydroxide. Extracting the mixture twice with 100 mL of ethyl acetate, followed by drying ($Na_2SO_4$), filtering and concentrating provided 5.3 g of the product as a yellow solid, mp 124°–126° C. $^1$H NMR (60 MHz, 20% DMSO $d_6$/$CDCl_3$) δ 8.05 (s, 1H, NH), 7.05 (d, J=8 Hz, 1H), 6.80 (d, J=2 Hz, 1H), 6.55 (dd, J=2, 8 Hz, 1H), 5.90 (broad s, 1H, indole CH), 2.40 (s, 3H).

b) 2-methyl-5-(4-sulfonatobutoxy)indole

To a mixture of 2.72 g (16.2 m mol) of toluene, washed 25% potassium hydride and 30 mL of DMSO was added 2.0 g (13.6 m mol) of 5-hydroxy-2-methyl indole. A solution of 11.5 g (54.5 m mol) of dibromobutane in 30 mL of DMSO was added dropwise over a 15 minute period. The reaction was stirred for 30 minutes and then diluted with 200 mL of 50% $CHCl_3$/water. The aqueous layer was extracted twice more with 100 mL of $CHCl_3$ whereupon the organic extracts were combined, dried with $Na_2SO_4$ and concentrated. The residue was chromatographed on 150 g of silica gel 60 and eluted with $CHCl_3$ to produce 1.1 g of 5-(4-bromobutoxy)-2-methyl indole as a white solid, mp 77°–79° C.

A mixture of 5.3 g (18.7 m mol) of 5-(4-bromobutoxy)-2 methyl indole, 2.6 g (20.6 m mol) of sodium sulfite in 50 mL of water were refluxed overnight and the supernatant liquid decanted while hot. After the solution cooled to room temperature, NaCl was added to the point where precipitation was observed. The mixture was filtered to yield a white solid which still contained some salt whereupon the solid was slurried in 70 mL of hot ethanol and the slurry filtered while hot. Upon cooling, a gelatinous mass was separated from the ethanol. Water was added until it dissolved and the solution was concentrated to a film. The residue crystallized under high vacuum to yield 2.1 g of product which contained 5% salt by weight. $^1$H NMR (3000 MHz, DMSO-$d_6$) δ 7.2 (d, J=8.5 Hz, 1H), 6.88 (d, J=2.3 Hz, 1H), 6.60 (dd, J=2.3, 8.5 Hz, 1H), 6.00 (t, J=1 Hz, 1H), 3.89 (t, J=6 Hz, 2H), 2.5 (t, J=7 Hz, 2H), 1.75 (m, 4H). $^{13}$C NMR (DMSO-$d_6$) δ 152.59, 136.11, 131.31, 129.19, 111.00, 102.47, 99.05, 67.98, 51.32, 28.50, 22.15, 13.55.

EXAMPLE II

Preparation of 5-(2-Sulfonatoethyl)-2-methylindole a) 4-(2-hydroxyethyl)phenylhydrazine hydrochloride A slurry of 5 g of 4-nitrophenethyl alcohol, 0.58 g of 10% Pd on carbon in 50 mL of absolute ethanol was shaken overnight under 50 psi of $H_2$. The mixture was filtered and concentrated to yield 3.6 g of 4-(2-hydroxyethyl) aniline, mp 101°–102° C.

A solution of 7.06 g (56.3 m mol) of the hydroxyethylaniline, 16.9 mL of concentrated HCl and 150 mL of water was prepared and cooled to 5° C. Sodium nitrate (4.08 g, 59 m mol) in 25 mL of water was added dropwise. After stirring for 15 minutes, excess $NaNO_3$ was destroyed by the addition of small portions of sulfamic acid, as determined by starch-iodide paper. This was then added dropwise to a 5° C. mixture of 48 g (218 m mol) of stannic chloride dihydrate in 48 mL of concentrated HCl. After warming to room temperature and stirring for 1 hour, the pH was adjusted to 5 with aqueous NaOH whereupon the solution was filtered and the pH lowered to 1.5 with aqueous HCl. At this point the mixture was concentrated and, periodically during the concentration, it was filtered to remove precipitated NaCl. Upon further concentration, the 3.6 g of the hydrazine hydrochloride precipitated out as a white crystalline solid, mp 194°–195° C. (dec). $^1$HNMR (60 MHz, DMSO-$d_6$) δ: 7.1 (d, 2H, J=8 Hz), 6.9 (d, 2H, J=8 Hz), 3.70 (large broad t, 12H, water NH and OCH$_2$), 2.70 (t, 2H, J=8 Hz).

b) 5-hydroxyethyl-2-methylindole

A mixture of 3.35 g of 4-(2-hydroxyethyl) phenyl hydrazine hydrochloride, 2.5 g of 2,2-dimethoxypropane, 5 mL of acetone and 2 mL of acetonitrile was prepared and allowed to stir for 2 hours at room temperature. Filtration produced 3.3 g of the hydrazone as a white solid, mp 122°–124° C. Without further purification, 2 g of the hydrazone was refluxed in 50 mL of concentrated HCl for 2 hours. The mixture was concentrated to a volume of 10 mL and then neutralized with aqueous $NaHCO_3$. The mixture was extracted with 100 mL of EtOAc, dried ($Na_2SO_4$), filtered and evaporated. The residue was chromatographed on 100% silica gel 60 and eluted with 5% $CH_3OH/CHCl_3$. Evaporation of the appropriate fractions produced 1.3 g of the product as a pale yellow oil. $^1$HNMR (60 MHz, $CDCl_3$) δ: 8.2 (broad s, 1H, NH), 7.3–6.6 (m, 3H, aromatic ring CH), 6.1 (broad s, 1H, indole ring CH), 3.8 (t, J=8 Hz, 2H, CH$_2$), 2.9 (t, J=8 Hz, 2H, CH$_2$), 2.3 (s, 3H, CH$_3$).

c) 2-methyl-5-(2-sulfonatoethyl)-indole

A mixture of 0.48 g (2.75 m mole) of the hydroxyethylindole, 0.37 g (1.3 m mole) of PBr$_3$ and 0.075 mL of pyridine in 10 mL of $CH_2Cl_2$ was stirred at room temperature for 6 hours. The reaction was diluted with 50 mL of $CH_2Cl_2$ and washed with aqueous sodium bicarbonate. The mixture was dried ($Na_2SO_4$), filtered and concentrated. Chromatography of the residue on 100 g of silica gel 60 produced 0.2 g of 5-(2-bromoethyl)-2-methylindone as a white solid, mp 100°–102° C. This was added to a mixture of 0.13 g (1.03 m mol of $Na_2SO_3$ and 1.4 mL of 3:1 water-DMF. After heating for 7 hours at 100° C., the mixture was concentrated to dryness and 5 ml of water added. The mixture was extracted once with $CHCl_3$ and the aqueous layer concentrated to a volume of about 2 mL. After salting out the product by the addition of small portions of NaCl, there was obtained 0.05 g of the 5-sulfonatoethyl indole as a white solid. $^1$H NMR (300 MHz, DMSO-$d_6$) δ: 10.8 (broad s, 1H, NH), 7.16 (s, 1H, aromatic H), 7.14 (d, J=8 Hz, aromatic H), 6.8 (dd, J=1.5, 8 Hz, 1H, aromatic H), 6.01 (s, 1H, indole CH), 2.89 (m, 2H, —O$_3$SCH$_2$), 2.66 (m, 2H, benzylic CH$_2$), 2.35 (s, 3H, CH$_3$). $^{13}$C NMR (DMSO-$d_6$) δ 135.48, 134.65, 130.95, 128.87, 120.48, 117.85, 110.30, 98.70, 54.19, 31.70, 13.40.

EXAMPLE III

A solution of 25 gm of 2-methyl-5-(4-sulfonatobutoxy) indole sodium salt in 1 liter of water is prepared and allowed to saturate a 15 cm×8 cm web of filter paper. The filter paper is air dried for 6 minutes at 100° C. A ⅔ inch by ⅔ inch portion of this paper is immersed in distilled water and shaken for 2 minutes. This solution is allowed to stand for an additional 28 minutes after which time the paper is removed. A dip and read reagent strip (Multistix®10 SG) is immersed in the solution, removed immediately after saturation and read 60 seconds later. The urobilinogen pad on the reagent strip changes color and is read visually and on a Clinitek® 200+ reflectance spectrophotometer after an additional 25 seconds. The indole test control is deemed to be satisfactory if the urobilinogen pad of the Multistix gives a reading of 1 mg/dL (1 Ehrlich unit/dL). Decodes are calculated on the Clinitek® 200+ using the algorithm:

Decode=(Reflectance @550/Reflectance @630)* 1000.

The correlation between the initial decode values and those taken after 6 hours indicates that the reconstituted control solution is stable over this period of time.

Referring to Table I, the mg/dL column represents the concentration of urobilinogen which corresponds to the observed decode values. Decode ranges for each concentration of urobilinogen were determined through contrived studies and clinical studies which were evaluated instrumentally by reference methods.

TABLE I

|  | Decode Initial | Decode 6 Hours | Urobilinogen mg/dL* |
| --- | --- | --- | --- |
| Check-Stix Control | 916 | 903 | 0.2 |
| Control + 100% Indole | 373 | 397 | 8.0 |
| Control + 33% Indole | 460 | 499 | 8.0 |
| Control + 20% Indole | 545 | 567 | 4.0 |

*Clinitek® 200+ Display Levels

From the above data, it can be determined that the method of the present invention can be used to prepare test control strips which, when placed in water, provide an indole solution which gives a reflectance reading which corresponds to a specific urobilinogen concentration.

EXAMPLE IV

The following experiment was performed for purposes of comparing 2,5-dimethyl indole (DMI), 2-methyl-5-methoxyindole (MMI) and 2-methyl-5-(4-sulfonatobutoxy) indole (SBMI) in terms of their ability to react with Ehrlich's reagent, i.e. p-dimethylaminobenzaldehyde and hydrochloric acid, in aqueous solution:

140 mg. of DMI, MMI or SBMI were placed in a 10 ml volumetric flask, distilled water, containing no surfactant, was added to the full line and the resultant was thoroughly mixed. The indole/water combination (100 µL), was, in each case, added to 12 ml of distilled water with thorough mixing to provide a resultant containing 0.116 mg/dL of the indole, each of which was contacted with a dip and read reagent strip (Multistix®10 SG from Miles Inc.) which was removed immediately after saturation and read 60 seconds later on a Clinitek® 200+ reflectance spectrophotometer. The stated concentration of DMI and MMI is that which would have resulted if they had completely dissolved. In reality these indoles are only slightly soluble, so the actual concentration is much less.

The particular indole is regarded as satisfactory if the urobilinogen pad on the Multistix gives a reading of at least 1 mg/dL=(1 Ehrlich unit/dL) since at a urobilinogen level of 1 EU/dL the change in color of the test strip is clearly discernible. Decodes are calculated on the Clinitek® 200+ using the algorithm:

Decode=(Reflectance @550/Reflectance @630)·1000.

The correspondence between Ehrlich Units per deciliter (EU/dL) and decode values as well as the decode values obtained with each of the 3 indoles tested as described above are set out in the following Table II.

TABLE II

| | | Indole Decode @ 0.116 mg/dL | | |
| --- | --- | --- | --- | --- |
| EU/dL | Decode | DMI | MMI | SBMI |
| 0.2 | 840+ | | | |
| 1.0 | 740–839 | 919* | 786–828* | 514–561* |
| 2.0 | 634–703 | | | |
| 4.0 | 504–633 | | | |
| 8.0 | 0–503 | | | |

*Mean value for 12 runs.

From the data presented in Table II, it can be determined that DMI and MMI are not suitable, by themselves, for use in the device claimed in the system of the present invention for testing the Ehrlich solution in the test strips because DMI tested well above the range for 1.0 EU/dL and MMI was at the upper end of this range.

The device claimed in this patent application and the method for using it in a test control method for the detection of p-dimethylaminobenzaldehyde or p-diethylaminobenzaldehyde require that the matrix material from which the device is prepared by contacted with a concentrated solution of the indole in order for it to release enough indole into an aqueous test medium upon rehydration to provide a response of at least 1.0 EU/dL. This result can be achieved with the use of SBMI as evidenced by Example III but cannot be achieved with DMI which doesn't provide the desired response even when its solution is directly contacted with the urobilinogen test strip or MMI whose solution just barely provides this response. Clearly, if the initial solution of DMI and MMI cannot provide a sufficient amount in solution upon rehydration to provide the desired response, or just barely so, a matrix material could not absorb an amount of these indoles to provide a sufficient amount in solution upon rehydration to cause the desired result of verifying the continued activity of the urobilinogen test strip.

The indoles of the present invention are very soluble in water and can be dissolved in a high enough concentration to impregnate filter paper and be reconstituted in water to provide a positive control for the urobilinogen reagent strips. Other indoles that reacted with the Ehrlich reagent in the test strips were either not sufficiently soluble in water, 2,5-dimethylindole; 5-methoxy-2-methylindole, indole-2-carboxylic acid; indole-3-acetic acid and 5-methoxyindole-3-acetic acid, i.e. reacted too slowly to be read instrumentally, i.e. 1-(4-sulfobutyl)-2-methylindole or interfered with reactions of other analytes in the control solution, i.e. 2-methylindole impregnated in toluene.

A related indole, 2-methylindole sulfonic acid, was found to be unsatisfactory because it did not react with p-dimethylaminobenzaldehyde.

What is claimed is:

1. A test control method for a reagent system containing p-dimethylaminobenzaldehyde comprising (a) combining the reagent system with an aqueous solution of an indole of the formula:

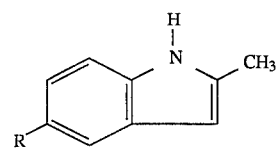

where R is $-(CH_2)_n SO_3^-$ wherein n is 2 to 6 or $-(OCH_2-(CH_2)_x)_m SO_3^-$ wherein X is 2 or 3 and m is 1 or 2 and (b) determining the formation of color in the aqueous solution.

2. The method of claim 1 wherein R is $-(CH_2)_n SO_3^-$ and n is 2 to 4.

3. The method of claim 2 wherein n is 4.

4. The method of claim 1 wherein the indole is provided in the form of a strip of a matrix material bearing a suitable quantity of the indole and is placed in an aqueous medium to provide the aqueous solution by dissolution.

5. The method of claim 4 wherein the matrix comprises filter paper.

6. A test strip for testing the efficacy of a composition containing p-dimethylaminobenzaldehyde which comprises a carrier matrix containing an indole of the formula:

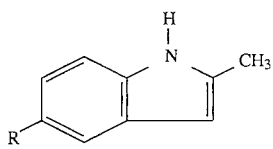

wherein R is $-(CH_2)_n SO_3^-$ wherein n is 2 to 6 or $-[OCH_2-(CH_2)_x]_m SO_3^-$ wherein X is 2 or 3 and m is 1 or 2.

7. The strip of claim 6 wherein n is 2 to 4.

8. The strip of claim 7 wherein n is 4.

9. The strip of claim 6 in which the carrier matrix is comprised of a bibulous material.

10. The strip of claim 9 wherein the bibulous material is filter paper.

11. A test control method for a reagent system containing p-dimethylaminobenzaldehyde or p-diethylaminobenzaldehyde which comprises combining the reagent system with a strip of a matrix material bearing a suitable quantity of 2-methyl-5-(4-sulfonatobutoxy) indole in an aqueous medium to cause the reagent system to undergo a colored response equivalent to at least about 1 Ehrlich Unit/dL.

12. The method of claim 1 wherein the matrix comprises filter paper.

13. A test strip for testing the efficacy of a composition containing p-dimethylaminobenzaldehyde or p-diethylaminobenzaldehyde as reagent which test strip comprises a carrier matrix containing 2-methyl-5-(4-sulfonatobutoxy) indole in sufficient quantity to cause the reagent to undergo a colored response equivalent to at least about 1 Ehrlich Unit/dL when the strip is rehydrated in an aqueous medium containing the reagent.

14. The test strip of claim 13 wherein the carrier matrix comprises filter paper.

* * * * *